United States Patent [19]
Jones et al.

[11] Patent Number: 5,436,361
[45] Date of Patent: Jul. 25, 1995

[54] PROCESS FOR SYNTHESIZING ENEDIYNES

[75] Inventors: Graham B. Jones, Clemson; Robert S. Huber, Central, both of S.C.

[73] Assignee: Clemson University, Clemson, S.C.

[21] Appl. No.: 231,232

[22] Filed: Apr. 22, 1994

[51] Int. Cl.$^6$ .............................. C07F 7/08; C07F 7/18
[52] U.S. Cl. ................... 556/466; 556/431; 556/465; 556/482; 556/489; 560/180; 549/20; 585/365; 585/446; 585/452; 585/457; 585/505; 585/534
[58] Field of Search ............... 556/466, 465, 431, 482, 556/489; 560/180; 549/20; 585/365, 446, 452, 457, 505, 534

[56] References Cited

U.S. PATENT DOCUMENTS

| | | | |
|---|---|---|---|
| 5,082,961 | 1/1992 | Fukumoto et al. | 556/466 |
| 5,231,205 | 7/1993 | Rieke | 556/466 X |
| 5,262,556 | 11/1993 | Riefling et al. | 556/466 X |

OTHER PUBLICATIONS

Zhou et al., Synthesis of Diacetylene Macrocyles Derived from 1,2-Diethynylbenzene . . . , 1294–1301, J. Org. Chem., 1994, 59.
Page 30, C&EN, Apr. 4, 1994.
Haseltine et al., Total Synthesis of Calicheamicinone: New Arrangement . . . , 3850–3866, J. Am. Chem. Soc., 1991, vol. 113.
Diederich et al., Complexes Incorporation Tetraphenyltetraethynylethene, pp. 205–208, J. Chem. Soc., Chem. Commun., 1994.
Vollhardt et al., Stereospecific Syntheses of Cis– and Trans–1,6–Bistrimethylsilyl– . . . , pp. 709–712, Tetrahydron Letters, vol. 26, No. 6, 1985, Great Britain.
Tarhouni et al., Monohalomethyllithium XCH$_2$Li: Stabilization . . . , pp. 835–838, Tetrahedron Letters, vol. 25, No. 8, Great Britain, 1984.
Andringa et al., Trimethylsilylation of Carbenoids Generated . . . , pp. C41–C43, Journal of Organometallic Chemistry, 336 (1987).
Seyferth et al., The Preparation of x–Halocyclopropyl Derivatives of Lithium . . . , pp. 255–286, Journal of Organometallic Chemistry, 88 (1975).
Crevisy, et al., "The Esperamicin–Calicheamicin Aglycones: Ring Closure of a Simple Strained System Medicated by Chronium (II)–Nickel (II) Salts", pp. 3171–3174, Tetrahydron Letters, 1991.
Semmelhack, et al., "Cyclic Conjugated Enediynes via Elimination of a Thionocarbonate in a Latent Z–hex-3–ene–1,5–diyne Unit", pp. 4121–4124, Tetrahedron Letters (1993).
Haseltine, et al., "Total Synthesis of Calicheamicinone: New Arrangement for Actuation of the Reductive Cyloaromatization of Aglycon Congeners", pp. 3850–3866, J. Am. Chem. Soc. (1991).
Vollhardt, et al., "Stereospecific Syntheses of Cis-and-Trans 1,6-bistrimethylsilyl-hex-3-ene-1,5-diyne", Tetrahedron Letters, vol. 26, No. 6, pp. 709–712 (1985).
Tarhouni, et al., "Monohalomethyllithium XCH$_2$Li: Stabilization of a Potential Synthetic Reagent", vol. 25, No. 8, pp. 835–838, Tetrahedron Letters (1984).
Andringa, et al., "Trimethylsilylation of Carbenoids Generated in Situ from Allyl and Benzyl Halides", pp. C41–C43, Journal of Organometallic Chemistry (1987).
Seyfreth, et al., "Halomethyl-Metal Compounds", Journal of Organometallic Chemistry, pp. 255–286 (1975).

*Primary Examiner*—Paul F. Shaver
*Attorney, Agent, or Firm*—Dority & Manning

[57] ABSTRACT

A process for synthesizing enediynes is provided. Specifically, the formed enediynes contain a hex-3-ene-1,5-diynyl group. Production of the enediynes involves adding a base to a propargylic halide in the presence of a chelating agent, which causes a carbenoid coupling-elimination sequence of the propargylic halides. A carbenoid destabilizing agent can also be added to the reaction mixture in order to enhance yield. Acyclic and cyclic enediynes can be synthesized according to this process. The enediynes are useful compounds that can be used in a variety of applications including use in the production of anti-tumor agents.

31 Claims, No Drawings

PROCESS FOR SYNTHESIZING ENEDIYNES

BACKGROUND OF THE INVENTION

The present invention generally relates to a process for producing enediynes and more specifically to a method for synthesizing enediynes containing a hex-3-ene-1,5-diynyl group.

Recently, much attention has focused on systems containing enediyne units as a result of their potential pharmaceutical applications. As used herein, an enediyne refers to a chemical compound containing a carbon double bond (ene) and a pair of carbon triple bonds (diyne). Specifically, enediynes have been incorporated into a number of bioactive agents. The bioactive agents have been studied primarily as antitumor agents in cancer chemotherapy trials.

One example of a possible anti-tumor drug containing an enediyne group is Calicheamicinone. As stated in an article by Haseltine et al. entitled "Total Synthesis of Calicheamicinone: New Arrangements for Actuation of the Reductive Cycloaromatization of Aglycon Congeners" published in *The Journal of the American Chemical Society*, Volume 113, pages 3850–3866, 1991, which is incorporated herein by reference in its entirety, Calicheamicinone has exhibited remarkably potent cytotoxicity and high cell-killing potential for cancer chemotherapy. In particular, Calicheamicinone and other similar chemical compounds containing enediynes possess DNA-damaging ability. Specifically, these compounds can cause strand scission of DNA via diyl radical attack.

The enediyne contained in Calicheamicinone represents the pharmacophore or active group responsible for its bioactive characteristics. Consequently, one of the components or constituents used in the synthesis of Calicheamicinone is a chemical compound containing the enediyne group and in particular, (Z)-1,6-dilithio-hex-3-ene-1,5-diyne. Unfortunately, this particular dilithio enediyne has been difficult and expensive to produce. In the past, synthesis of dilithio enediynes has been accomplished by first using a procedure derived by Vollhardt et al. as detailed in an article entitled "Stereospecific Synthesis of Cis- and Trans-1,6-Bistrimethylsilyl-Hex-3-Ene-1,5-Diyne" published in *Tetrahedron Letters*, volume 26, pages 709–712, 1985. Vollhardt et al. more particularly details the synthesis of isomers of 1,6-[bis(trimethylsilyl)]-hex-3-ene-1,5-diyne which is a precursor to the dilithio enediynes in a more protected form. The synthesis of enediynes in Vollhardt et al. includes a palladium-catalized reaction of substituted alkynes and vinyl halides. Specifically, the 1,6-[bis(trimethylsily)]-hex-3-ene-1,5-diynes are made through a catalytic double coupling of trimethylsilylethyne with isomers of dichloroethene. However, this method renders practical scale synthesis prohibitively expensive. Also, environmentally damaging compounds, such as organo chlorine compounds, must be used during synthesis of the enediynes. Consequently, a need exists for an efficient and inexpensive route to producing the needed enediynes.

Besides being used in anti-tumor agents, enediynes have also been found useful in a wide variety of other applications. For instance, enediynes also represent an important class of conjugated $\pi$ systems with potentially useful optical and electronic properties. Such uses are described by Diederich et al. in "$\pi$-Complexes Incorporating Tetraphenyltetraethynylethene" published in *The Journal of the Chemical Society, Chemical Communication*, pages 205–208, 1994, and incorporated herein by reference in its entirety. However, an efficient reaction scheme for synthesizing enediynes needed in such applications has remained absent from the prior art.

Various enediynes as can be produced by the process of the present invention have also been found useful in the synthesis of polymers and in the synthesis of substituted benzenes. Further uses are disclosed in "Synthesis of Diacetylene Macrocycles Derived from 1,2-Diethynylbenzene Derivatives: Structure and Reactivity of the Strained Cyclic Dimer" by Zhou et al. published in the *Journal of Organic Chemistry*, pp 1294–1301, 1994, which also is incorporated herein by reference.

SUMMARY OF THE INVENTION

The present invention recognizes and addresses the foregoing disadvantages, and others of prior art constructions and methods.

Accordingly, it is another object of the present invention to provide a method for synthesizing chemical compounds containing the hex-3-ene-1,5-diynyl group.

It is another object of the present invention to provide a process for making chemical compounds used in antitumor agent design.

Another object of the present invention is to provide an improved method for synthesizing 1,6-[bis(trimethylsilyl)]-hex-3-ene-1,5-diyne.

It is another object of the present invention to provide a process for synthesizing cyclic enediynes.

Still another object of the present invention is to provide a method of synthesizing enediynes through a carbenoid coupling reaction.

These and other objects of the present invention are achieved by providing a method for synthesizing enediynes. The method includes the steps of providing a composition which contains a base. The composition is combined with a propargylic halide in the presence of a chelating agent. During addition of the composition, a proportionate amount of the propargylic halide undergoes deprotonation transforming the proportionate amount into a monhalocarbenoid. The monohalocarbenoid couples with the remainder of the propargylic halide to form an intermediate halo-diyne which then eliminates a hydrogen and halide in situ to form the enediyne. Specifically, the formed enediyne contains a hex-3-ene-1,5-diynyl group.

The process can further include the step of adding a carbenoid destabilizing agent such as hexamethylphosphortriamide (HMPA) to the composition. Bases suitable for use in the process include LHMDS, LTMP, or LDA. A chelating agent that can be added to the mixture is THF and the reaction can occur at temperatures between about 25° C. to about −95° C.

In one embodiment, the propargylic halide can be a trimethylsilylpropargyl halide and wherein the formed enediyne is a 1,6-[bis(trimethylsilyl)]-hex-3-ene-1,5-diyne. In another example, the propargylic halide can be a phenyl propargylic halide and the formed enediyne is a 1,6-diphenyl-hex-3-ene-1,5-diyne. The propargylic halide can also be 1,10-dibromodeca-2,8-diyne forming cyclodec-2-en-1,3-diyne.

These and other objects are also accomplished by providing a process for synthesizing an enediyne. The process includes the steps of combining a nonnucleophylic lithium base with a carbenoid destabilizing agent to form a chemical composition. The composition is added to a propargylic halide in the presence of a chelating agent. The propargylic halide can be represented by the following formula:

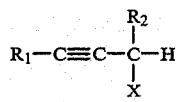

wherein X is Cl, Br or I; and $R_1$ and $R_2$ are nonfunctional groups. The corresponding enediyne produced is as follows:

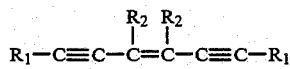

Again, the lithium base can include LHMDS, LTMP, or LDA and the carbenoid destabilizing agent can be HMPA. The molar ratio of the carbenoid destabilizing agent to the lithium base is about 1 or less. Further, the molar ratio of the lithium base to propargylic halide is about 1 or greater. The chelating agent can be THF or ether. The rate of addition of the reagent to the propargylic halide can be between about 0.5 equivalents per hour to about 1.5 equivalents per hour of the lithium base in relation to the propargylic halide.

From the above formulas, $R_1$ can include hydrogen, an alkyl group, an alkenyl group, an alkynyl group, an aryl group, or a trialkylsilyl group. Specifically, $R_1$ can be TMS or a phenyl group.

In a process for synthesizing cyclic enediynes, the process can include the steps of combining a chelating agent with a propargylic halide to form a solution. The propargylic halide can have the following formula:

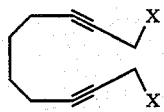

wherein X is chlorine, bromine or iodine. A base and a carbenoid destabilizing agent are added to the solution at a rate sufficient to promote the production of an enediyne having the following formula:

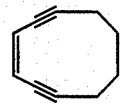

The process can be carried out at various temperatures such as between about 25° C. to about −95° C.

Other objects, features and aspects of the present invention are discussed in greater detail below.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to the synthesis and production of enediynes. In particular, the enediynes contain a hex-3-ene-1,5-diynyl group in either a cis (Z) or a trans (E) configuration. The synthesized enediynes possess many desirable characteristics and can be used in a wide variety of applications. As discussed above, the enediynes can be used as pharmacophores for a number of bioactive anti-tumor model systems. The enediynes could also be used for polymer synthesis, for synthesis of substituted benzenes or for applications optimizing their electrical and electronic properties.

In general, the enediynes are prepared by adding a deprotonating base and preferably a hindered nonnucleophilic lithium base to a propargylic halide in the presence of a solvent or chelating agent. The resulting reaction scheme can be broadly represented as follows for acyclic products:

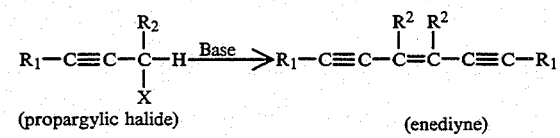

wherein X is chlorine, bromine or iodine.

In particular, it is believed that while the base is being added, a proportionate amount of the propargylic halide is transformed into a carbenoid and specifically a monohalocarbenoid via a deprotonation. The monohalocarbenoids, once formed, immediately couple with a propagylic halide that has not undergone deprotonation (non-lithiated molecules). During coupling, the following intermediate is believed to be formed:

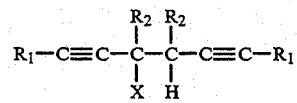

which rapidly undergoes an elimination of the hydrogen and the halide to produce the desired enediyne.

Practically any propargylic halide or mixtures thereof can be used in the process of the present invention. A propargylic halide as used herein refers to any chemical compound containing a three carbon chain in which there appears a triple bond between the first and second carbon atoms and in which a hydrogen and a halide are bonded to the third carbon atom. One particular group of propargylic halides that can be used in the process of the present invention is represented above. As shown, the propargylic halide contains two chemical groups denoted $R_1$ and $R_2$. These groups are generally nonfunctional groups that do not play a role or have an active part in synthesizing the enediynes. As used herein, a nonfunctional group is defined as a chemical group that does not undergo a chemical change during the reaction and that does not adversely interfere with production of the desired enediyne. The hydrogen and halide bonded to the end carbon atom, on the other hand, are necessary for the carbenoid coupling and elimination sequence.

Merely for purposes of description but not limitation, $R_1$ can be represented by reference to generic classes of chemical groups. In particular, $R_1$ can be an alkyl group, an alkenyl group, an alkynyl group, an aryl group or a trialkylsilyl group. As used herein, the above referenced chemical groups not only refer to particular hydrocarbon chains but also to any other additional chemical groups attached thereto. Further, $R_1$ can be a combination of any of the above described groups in any particular order. In general, $R_1$ can be practically any type of carbon chain and preferably a carbon chain containing 20 carbon atoms or less. Perhaps the only limitation that can be placed on the $R_1$ group is that it should not be reactive with the base added to the propargylic halide to an extent that would cause interference with the production of the enediyne or adversely interfere with the reactivity of the carbenoids.

For exemplary purposes, if $R_1$ were a alkyl group, $R_1$ could be a methyl, ethyl or propyl group with any additional nonfunctional chemical groups attached thereto. Similarly, if $R_1$ were an alkenyl or an alkynyl group, $R_1$ could be any short to long chain hydrocarbon containing the appropriate double or triple bond. Again, further chemical groups may be attached thereto. Also, if $R_1$ were an aryl group, $R_1$ can include a phenyl group or can be represented by a substituted benzene.

In one particularly useful application, $R_1$ can be a trialkylsilyl group such as a trimethylsilyl group (TMS). The resulting enediynes produced when $R_1$ is a TMS group are the Z and E isomers of 1,6-[bis(trimethysilyl)]-hex-3-ene-1,5-diyne. These enediynes can be used in many applications including the production of anti-tumor agents. Specifically, (Z)-1,6-[bis(trimethysilyl)]-hex-3-ene-1,5-diyne can be easily converted to a dilithio salt by first removing the TMS groups by base catalysis and then titrating with n-butyl lithium as described in Haseltine et al. The resulting dilithio enediyne can be used to produce a number of bioactive enediyne anti-tumor agents including derivatives of Calicheamicinone as discussed above.

Similar to the $R_1$ group, the other nonfunctional group contained in the above represented propargylic halide, $R_2$, can also include a broad range of chemical groups. Again, the only requirement is that the $R_2$ group not interfere significantly with the carbenoid coupling reaction in producing the desired enedynes. Specifically, $R_2$ can be a hydrogen, an alkyl group, or an alkynyl group. In particular, experiments performed wherein $R_2$ was an ethyl group or an alkynyl group in combination with a phenyl group proved successful.

In summary, a wide variety of different chemical groups can be substituted for $R_1$ and $R_2$ in the above-described propargylic halide. Selection of an appropriate $R_1$ or $R_2$ group depends on the particular application of the resulting enediyne. In particular, $R_1$ and $R_2$ can be chosen so as to later facilitate synthesis of other chemicals using the produced enediyne. Also, desired physical characteristics can be incorporated into the enediynes by choosing appropriate nonfunctional groups.

As described above, a deprotonating base and preferably a nonnucleophilic lithium base is added to the propargylic halide in order to initiate the carbenoid coupling sequence. Such lithio amide bases can include lithio tetramethylpiperidine (LTMP), lithio hexamethyldisilylamide (LHMDS), and lithium diisopropylamide (LDA). Other bases such as butyl lithium (BuLi) and sodium hydride may also be used. However, these bases have been tested and have been found not to work to any significant degree. Of the above listed bases, LHMDS has been found to be the most preferred.

In a preferred embodiment, the base is added to the propargylic halide very slowly in order to maximize enediyne production. For instance, for smaller reactions, the base is added in a dropwise manner. Although not necessary, the rate of addition of base to propargylic halide can be from about 0.5 equivalents per hour to about 1.5 equivalents per hour. Also, the molar ratio of base to halide contained within the propargylic halide in the final solution should be at least about 1 to 1 for a complete reaction. Excess base such as in a ratio of 5 to 1 can also be used but has been found not to provide any significant benefit.

Preferably, the base is added to the propargylic halide in the presence of a chelating agent or solvent. A chelating agent is a chemical compound in which atoms form coordinate bonds with metals in the solution. Chelating agents that have been found useful in the present invention include tetrahydrofuran (THF) or ether. Both of these chemicals are a liquid at room temperature and have very low freezing points. Hexanes have also been tried but have found to reduce production of the desired product. Preferably, THF is chosen as the solvent simply because the propargylic halides are more soluble therein at lower temperatures.

The temperature of the propargylic halide prior to addition of the nonnucleophylic lithium base can also play a factor in the rate of reaction and yield of product. In general, the reaction can be carried out at temperatures between about 25° C. and about −95° C. However, the reaction is best carried out at lower temperatures. For synthesizing acyclic enediynes, preferably the temperature of the propargylic halide or reaction solution is between about −75° C. and about −95° C. For cyclic enediynes, the propargylic halide is preferably between 25° C. and about −40° C. Although these temperature ranges are preferred, they are not critical to the general reaction scheme. In fact, in commercial applications it may be more economical to run the reaction closer to ambient temperature.

In order to improve yield, a carbenoid destabilizing agent can also be added to the reaction mixture of the present invention. In general, a carbenoid destabilizing agent causes newly formed carbenoids to immediately couple to a propargylic halide. Although unknown, it is believed that as the carbenoid coupling reaction proceeds the lithium ion contained in the base combines with the eliminated halide to produce lithium halide compounds that have a stabilizing effect on carbenoids. If the rate of coupling decreases substantially, all of the available propargylic halide will be lithiated, creating a deficit of propargylic halide for coupling to the formed carbenoids. Addition of a carbenoid destabilizing agent reverses the effect of any lithium halide present in the reaction mixture.

A preferred carbenoid destabilizing agent is hexamethylphosphortriamide (HMPA). Preferably, HMPA is combined with the base before being added to the propargylic halide. The molar ratio of the carbenoid destabilizing agent to the base should be around 1.0 and preferably does not exceed 1. If excess HMPA is present in the reaction medium, degradive processes can occur causing the carbenoids to become overactive and competitive which may lead to the formation of undesired side products. The process of the present invention synthesizes various enediynes. The final product may include isomers of a particular enediyne. Specifically, cis (Z) and trans (E) isomers can be synthesized in calculated ratios. For the most part, these isomers can be easily separated and used in different processes as desired.

In one embodiment of the process of the present invention, a mixture of different propargylic halides can be coupled together. Such a reaction scheme can be represented as follows:

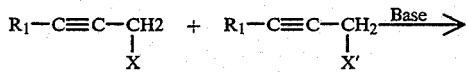

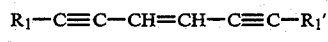

wherein X and X' are Br, Cl, or I and R$_1$ and R$_1$' are nonfunctional groups as described above. In this particular reaction scheme, coupling of each propargylic halide to itself may also occur.

Utilizing the process of the present invention, cyclic enediynes can also be produced which are particularly useful in the production of anticancer agents. While the reaction conditions, the constituents, and the reaction mechanism is generally the same, the following equation represents a general reaction sequence for the production of cyclic enediynes:

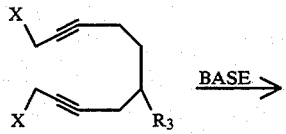

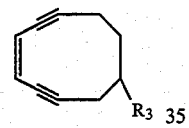

wherein X is chlorine, bromine or iodine and R$_3$ is a nonfunctional group. In producing cyclic enediynes, a dihalide is generally needed which also means that two equivalents of base are needed for a full reaction. However, again the reaction mechanism is generally the same.

The R$_3$ group shown above can include hydrogen or a desired non-functional group. Specifically, a chemical group can be chosen for substitution with R$_3$ that will enhance the utility of the resulting cyclic enediyne. For instance, the R$_3$ group can be used in the resulting enediyne for reaction with other chemical compounds in the production of needed pharmaceuticals.

The following is a list of acyclic and cyclic enediynes that have been synthesized through the reaction mechanism and process of the present invention. The following is a list of possible resulting compounds. The list is not exhaustive but is merely provided for illustrative purposes.

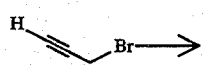

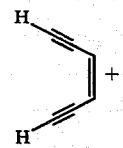

-continued

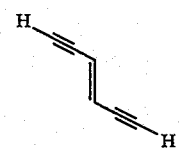

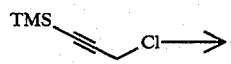

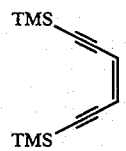

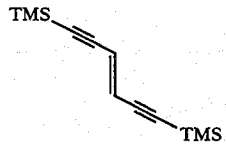

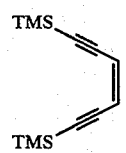

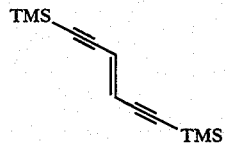

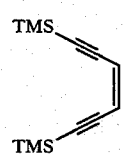

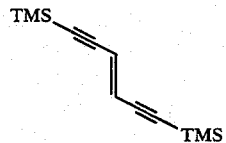

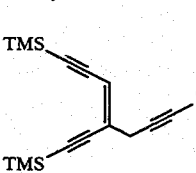

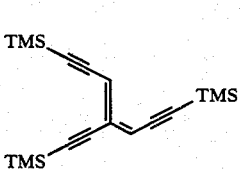

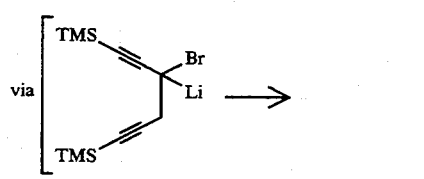
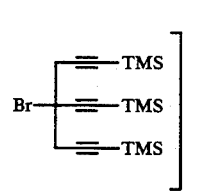
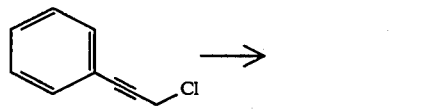
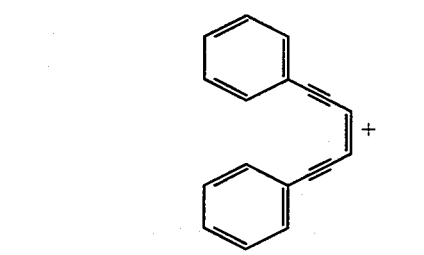
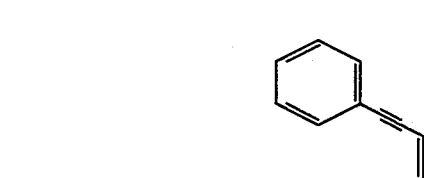
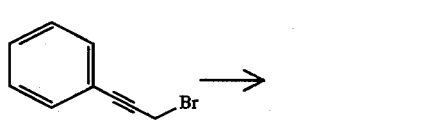
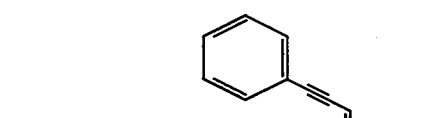
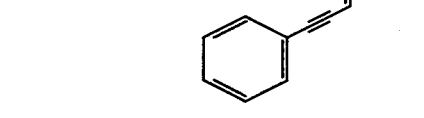

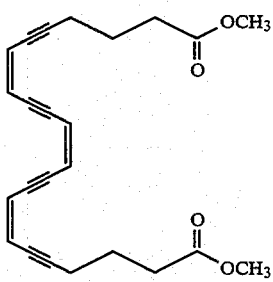
+
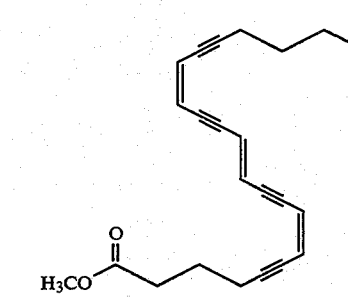
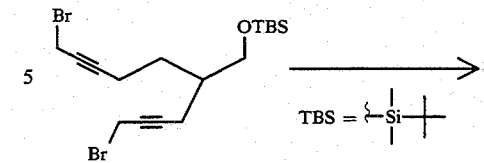
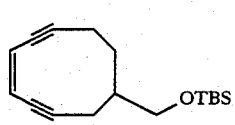
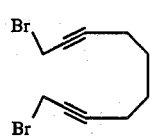
→
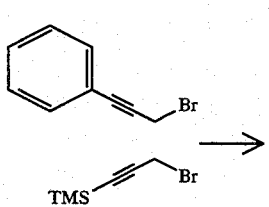
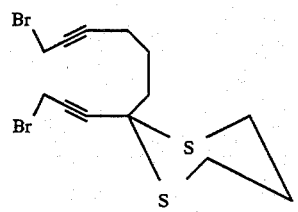
→
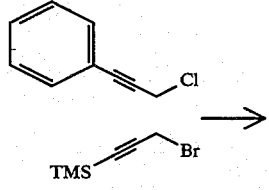
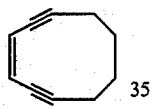
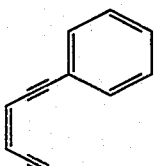
+
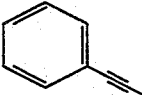
+ bis-phenyl(E/Z isomers)
+ bis-TMS(E/Z isomers)
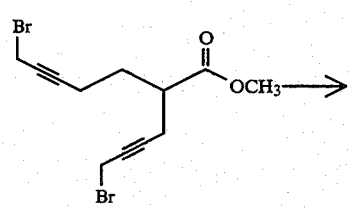
→
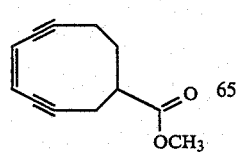
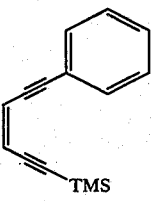
+
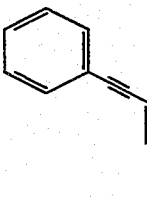
+ bis-phenyl(E/Z isomers)
+ bis-TMS(E/Z isomers)

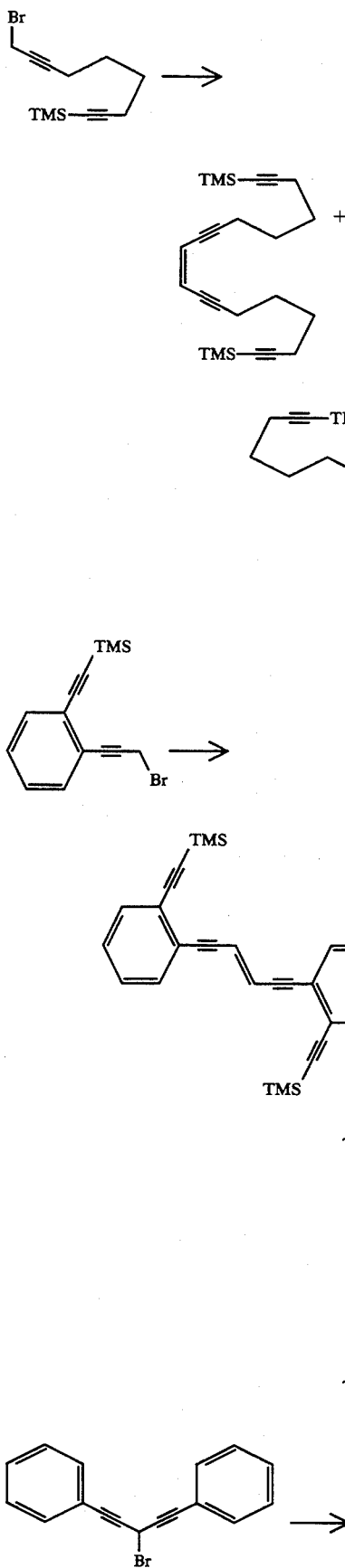

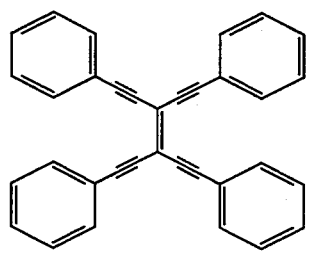

The present invention may be better understood by reference to the following examples.

EXAMPLE 1

The following procedure was developed in order to synthesize the (Z) and (E) isomers of 1,6-[bis (trimethylsilyl)]-hex-3-ene-1,5-diyne from trimethylsilylpropargyl bromide. 1,6-[bis(trimethylsilyl)]-hex-3-ene-1,5-diyne can be represented as:

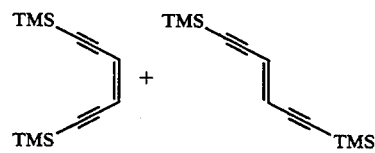

1.15 mL of a solution of HMDS (5.5 mmol) was added to 10 mL of THF and cooled to −10° C. 2.03 mL of 2.71M BuLi was added dropwise. After 0.5 h, 0.96 mL (5.5 mmol) of HMPA was added and the resulting solution was allowed to stir for an additional 5 min. before it was transferred by cannula over the course of 2.0 h (rate=0.55 equiv./hr) to a magnetically stirred solution of 0.956 g (5.0 mmol) of trimethylsilylpropargyl bromide in 20 mL THF at −92° C. (bath temp.). The trimethylsilylpropargyl bromide was obtained from the Aldrich Co. in Milwaukee, Wis.

Upon completion of the base addition, the resulting enediyne solution was allowed to stir for a further 10 min. at −92° C. before it was poured, without warming, onto a slurry of crushed ice and saturated NH4Cl. The product was extracted into ether and the ether extracts were washed successively with 10% HCl, H2O, sat. NaHCO3, and brine and then concentrated. Flash chromatography on silica gel (0 to 2% Et2O/hexane) gave 0.154 g (28%) of the trans isomer as white crystals and 0.331 g (60%) of the cis isomer as a colorless oil.

EXAMPLE 2

Trimethysilylpropargyl chloride was prepared from the commercially available trimethylsilylpropargyl bromide. Specifically, a simple halogen exchange was performed by combining trimethylsilylpropargyl bromide with excess lithium chloride (LiCl) in refluxing acetone.

EXAMPLE 3

The procedure described in Example 1 was followed using the trimethylsilylpropargyl chloride as prepared in Example 2. In particular, 1,467 g of trimethylsilylpropargyl chloride (10.0 mmol) produced 0.89 g (80%) of 1,6-[bis(trimethylsilyl)]-hex-3-ene-1,5-diyne. The (Z) to (E) ratio of the resulting product was 1.9:1.0. A small amount of the starting halide was found to be present in the crude product.

EXAMPLE 4

Trimethylsilylpropargyl iodide was also prepared from the commercially available bromide. Again, a simple halogen exchange was performed by combining trimethylsilypropargyl bromide with excess sodium iodide (NaI) in refluxing acetone.

EXAMPLE 5

The procedure described in example 1 was followed using the trimethylsilylpropargyl iodide as prepared in Example 4. In particular, 1.352 grams of trimethylsilylpropargyl iodide (5.68 mmol) produced 0.575 g (91%) of 1,6-[bis(trimethylsilyl)]-hex-3-ene-1,5-diyne. The (Z) to (E) ratio of the resulting product was 1.83:1.0. In this case, the reaction mixture became extremely black during the course of the base addition. NMR analysis of the crude product, however, showed it to be extremely clean and free of the starting materials.

EXAMPLE 6

Using procedures similar to that described in Example 1, the following table was compiled representing attempts to couple trimethylsilylpropargyl bromide using various lithium bases.

| Trial No. | Base | Molar Ratio of base to Reactant | Solvent | % Conversion | % Yield | Z:E Ratio |
|---|---|---|---|---|---|---|
| 1 | BuLi | 1.1 | THF | Trace | Trace | — |
| 2 | LDA | 1.0 | THF | Trace | <10 | 1:1 |
| 3 | LDA | 0.5 | THF | 15.6 | 30 | 1:2.32 |
| 4 | LDA | 0.25 | THF | Trace | Trace | — |
| 5 | LiHMDS | 0.25 | THF | 43.7 | 85 | 2.24:1 |
| 6 | LiHMDS | 2.0 | THF | 94 | 94 | 2.15:1 |
| 7 | LiHMDS | 1.1 | THF | 67 | 64 | 1.93:1 |
| 8 | LiHMDS | 1.1 | Hex./THF | 3 | Trace | — |
| 9 | LiHMDS | 1.1 | THF/HMPA | 100 | 96 | 2.11:1 |

EXAMPLE 7

Preparation of:

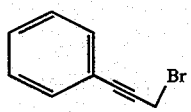

In order to produce 1,6-diphenyl-hex-3-ene-1,5-diyne, phenylpropargyl bromide was first prepared. 7.56 g of phenylacetylene (74 mmol) was dissolved in 200 mL of Et$_2$O and cooled to −78° C. 30 mL of butyllithium (2.7M) was added dropwise and the resulting solution was allowed to stir for 1.0 hr at −78° C. 6.66 g of the aldehyde, paraformaldehyde, (222 mmol) was added and the resulting solution was stirred for 2.0 hr at 0° C. Addition of 100 mL of sat. NH$_4$Cl followed, and the product alcohol extracted with diethyl ether. The solvents were evaporated, and the crude alcohol was added to a 0° C. solution of 81 mmol of Ph$_3$P:Br$_2$ (prepared from 12.95 grams of bromine and 21.2 grams of Ph$_3$P) in 200 mL of CH$_2$Cl$_2$. After 20 minutes at this temperature, 200 mL of pentane was added and the product filtered through a short bed of silica. Dry column flash chromatography (pentane eluent) gave the desired bromide, sufficiently pure for carbenoid coupling.

EXAMPLE 8

Synthesis of:

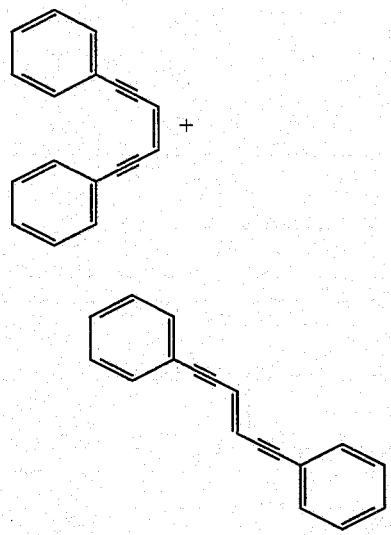

1,6-diphenyl-hex-3-ene-1,5-diyne was produced as follows.

4.0 mL of 2.7M BuLi was added dropwise to a solution of 1.77 g of HMDS in 20 mL of THF cooled to −10° C. 1.97 g of HMPA (11.0 mmol) was added. The resulting solution containing the base, LHMDS, was added to a −90° C. solution of phenylpropargyl bromide as prepared in Example 7 over the course of 2 hr. The phenylpropargyl bromide solution contained 1.95 g of phenypropargyl bromide (10.0 mmol) in 40 mL of THF. The reaction medium had a green coloration which gradually deepened in color during the addition of the base.

1.17 g Of 1,6-diphenyl-hex-3-ene-1,5-diyne was produced with a Z to E ratio Of 1:1. The yield was 100%.

EXAMPLE 9

Preparation of:

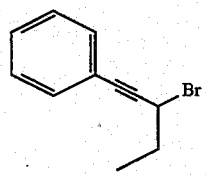

The above propargylic bromide was prepared following the procedure described in Example 7. However, instead of paraformaldehyde, 16 mL (222 mmol) of the aldehyde, CH$_3$CH$_2$CHO was added. Again, the above propargylic bromide was produced sufficiently pure for carbenoid coupling.

EXAMPLE 10

Synthesis of:

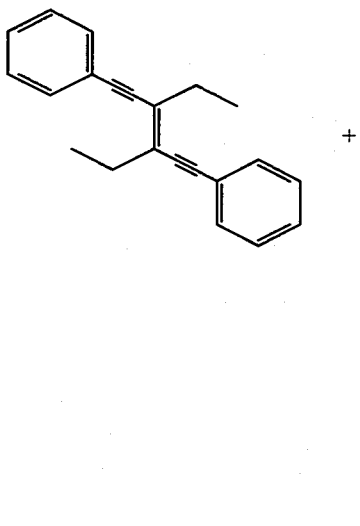

+

The above enediyne was synthesized according to the procedure described in Example 8. 2.23 g (10.0 mmol) of the propargylic bromide prepared in Example 9 (3-bromo-1-pheylpentyne) yielded 0.284 g (20%) of the above enediyne following column chromatography (2:98, Et₂O:hexane). The (Z) to (E) ratio was 1:1.

EXAMPLE 11

Preparation of:

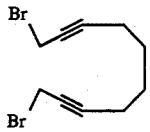

In order to produce cyclodec-2-en-1,3-diyne, 1,10 dibromodeca-2,8-diyne was first prepared.

2.12 g of commercially available 1,7 octadiyne (20.0 mmol) was first combined with 80 mL of Et₂O and 30 mL of THF. The solution was cooled to −78° C. and treated with 15.6 mL (42 mmol, 2.7M) of BuLi. After 0.5 hr at this temperature, 4.8 g of paraformaldehyde (160 mmol) was added and stirred for a further 2.0 hr at 0° C. At 10% soln. of aqueous HCl was added and the crude product extracted into diethyl ether. Treatment of the ether extracts with sat. NaHCO₃ and brine, followed by solvent removal and column chromatography (60:40 EtOAc: Hexane) gave pure deca-2,8-diyne-1,10-diol in 50% yield.

1.67 g of the diol described above (10 mmol) was dissolved in 20 mL of CH₂Cl₂ and this solution was added to a 0° C. solution of Ph₃P:Br₂ (24 mmol) in 50 mL of CH₂Cl₂. After 0.5 hr, 100 mL of pentane was added and the reaction mixture was filtered through a short bed of silica. Solvent removal gave 2.9 grams (100%) of the desired dibromide which was found by NMR to be sufficiently pure to proceed with the carbenoid coupling protocol.

EXAMPLE 12

Synthesis of:

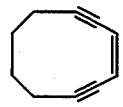

Cyclodec-2-en-1,3-diyne was produced as follows.

0.146 g of 1,10-Dibromo-2,8-decadiyne (0.5 mmol) as prepared in Example 11 was dissolved in 40 mL of THF, cooled to −40° C., and treated over the course of 2.0 hr with a solution of 1.5 mmol of LHMDS (from 0.55 mL of 2.7M BuLi and 0.242 grams of HMDS), and HMPA (0.269 grams, 1.5 mmol) in 10 mL of THF. The reaction mixture was then poured onto a slurry of crushed ice and saturated NH₄Cl. The product was extracted into ether and the ether extracts were washed successively with 10% HCl, H₂O, saturated NaHCO₃ and brine. The extracts were then concentrated. Column chromatography (0–4% Et₂O hexane) yielded 13 mg (20%) of the above desired enediyne.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to be limitative of the invention so further described in such appended claims.

What is claimed is:

1. A process for synthesizing enediynes, said process comprising the steps of:
   a) providing a composition, said composition containing a deprotonating base; and
   b) combining said composition with a propargylic halide in the presence of a chelating agent, wherein a proportionate amount of said propargylic halide undergoes deprotonation transforming said proportionate amount into a monohalocarbenoid, said monohalocarbenoid coupling with the remainder of said propargylic halide to ultimately form an enediyne, said enediyne containing a hex-3-ene-1,5-diynyl group.

2. The process as defined in claim 1, wherein said propargylic halide is at a temperature between about 25° C. and about −95° C. when combined with said composition.

3. The process as defined in claim 1, further comprising the step of adding a carbenoid destabilizing agent to said composition.

4. The process as defined in claim 3, wherein said carbenoid destabilizing agent comprises HMPA and wherein the molar ratio of said carbenoid destabilizing agent to said base is about 1 or less.

5. The process as defined in claim 1, wherein said base is LHMDS, LTMP, LDA or butyl lithium.

6. The process as defined in claim 1, wherein the molar ratio of said base to said propargylic halide is from about 1 to about 5.

7. The process as defined in claim 1, wherein said propargylic halide is a trimethylsilylpropargyl halide and said formed enediyne is a 1,6-[bis (trimethylsilyl]-hex-3-ene-1,5-diyne.

8. The process as defined in claim 1, wherein said propargylic halide is a phenylpropargyl halide and said formed enediyne is a 1,6-diphenyl-hex-3-ene-1,5-diyne.

9. The process as defined in claim 1, wherein said propargylic halide is 1,10-dibromodeca-2,8-diyne and said formed enediyne is cyclodec-2-en-1,3-diyne.

10. The process as defined in claim 1, wherein said chelating agent comprises THF.

11. A process for synthesizing an enediyne, said process comprising the step of:
reacting a propargylic halide in the presence of a lithium base, a carbenoid destabilizing agent and a chelating agent to form an enediyne, said propargylic halide having the following formula:

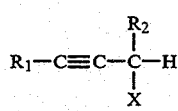

wherein X is Cl, Br, or I; and $R_1$ and $R_2$ are nonfunctional groups; and wherein an enediyne is produced having the following formula:

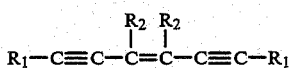

12. The process as defined in claim 11, wherein said lithium base is LHMDS, LTMP, LDA or butyl lithium.

13. The process as defined in claim 11, wherein said carbenoid destabilizing agent comprises HMPA and wherein the molar ratio of said carbenoid destabilizing agent to said lithium base is about 1 or less.

14. The process as defined in claim 11, wherein said chelating agent is THF or ether.

15. The process as defined in claim 11, wherein $R_1$ is a trimethylsilyl group, $R_2$ is hydrogen and said produced enediynes are the Z and E isomers of 1,6-bis(trimethylsilyl)]-hex-3-ene-1,5-diyne.

16. The process as defined in claim 11, wherein $R_1$ is a phenyl group for producing enediynes having the following formula:

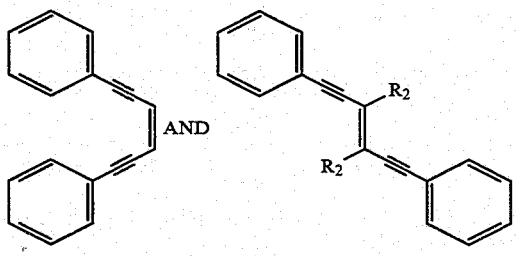

17. The process as defined in claim 11, wherein said propargylic halide has the following formula:

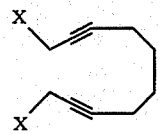

and said respective produced enediyne has the following formula:

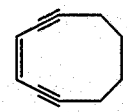

18. A process for making enediynes containing a hex-3-ene-1,5-diynyl group via a carbenoid coupling reaction, said process comprising the steps of:
a) preparing a chemical composition comprising a nonnucleophilic lithium base and hexamethylphosphortriamide, wherein the molar ratio of said hexamethylphosphortriamide to said base is about 1 or less; and
b) combining said composition with a solution comprising a chelating agent and a propargylic halide, said propargylic halide having the following formula:

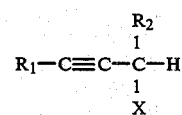

wherein X is Cl, Br, or I; $R_2$ is hydrogen, an alkyl group, or a alkynyl group; and $R_1$ is hydrogen, an alkyl group, an alkenyl group, an alkynyl group, an aryl group, or a trialkylsilyl group, and wherein enediynes are produced having the following formula:

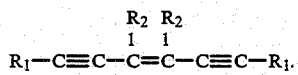

19. The process as defined in claim 18, wherein said composition is added to said propargylic halide at a rate of between about 0.5 equivalents per hour to about 1.5 equivalents per hour of said lithium base.

20. The process as defined in claim 18, wherein said nonnucleophilic lithium base is LHMDS, LTMP, or LDA.

21. The process as defined in claim 18, wherein the molar ratio of said nonnucleophilic lithium base to said propargylic halide is from about 1 to about 5.

22. The process as defined in claim 18, wherein said propargylic halide is:

and wherein said produced enediynes are the following Z and E isomers:

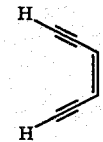

and

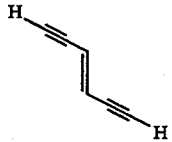

23. The process as defined in claim 18, wherein said propargylic halide is:

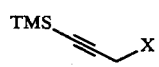

and wherein said produced enediynes are the following Z and E isomers:

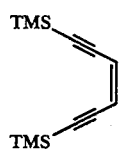

and

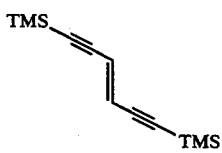

24. The process as defined in claim 18, wherein said propargylic halide is:

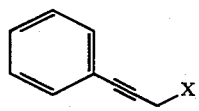

and wherein said produced enediynes are the following Z and E isomers:

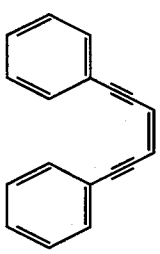

and

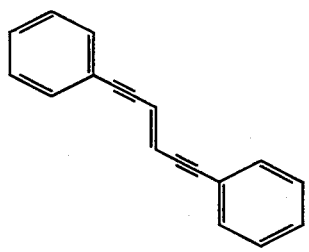

25. The process as defined in claim 18, wherein said propargylic halide is:

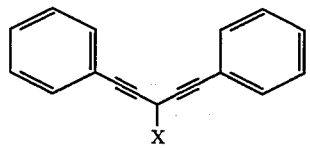

and said produced enediyne is:

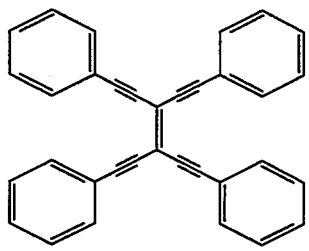

26. The process as defined in claim 18, wherein said solution comprises a second propargylic halide for coupling to said first propargylic halide, said second propargylic halide having the following formula:

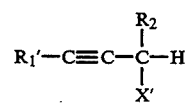

wherein $X'$ is Cl, Br, or I and $R_1'$ is hydrogen, an alkyl group, an alkenyl group, an alkynyl group, an aryl group, or a trialkylsilyl group, and wherein enediynes are produced having the following formula:

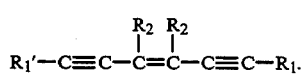

27. A process for synthesizing cyclic enediynes, said process comprising the steps of:
   a) combining a chelating agent with a propargylic halide to form a solution, said propargylic halide having the following formula:

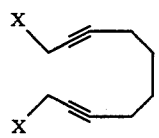

wherein X is Cl, Br or I; and
   b) adding to said solution a nonnucleophilic lithium base and a carbenoid destabilizing agent at a rate sufficient to promote the production of a cyclic enediyne, said enediyne having the following formula:

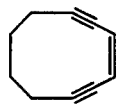

28. The process as defined in claim 27, wherein said propargylic halide is:

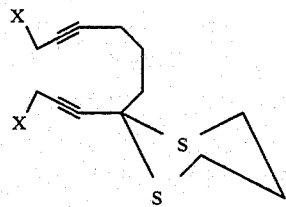

and said corresponding produced cyclic enediyne is:

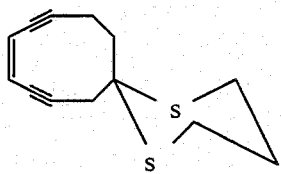

29. The process as defined in claim 27, wherein said propargylic halide is:

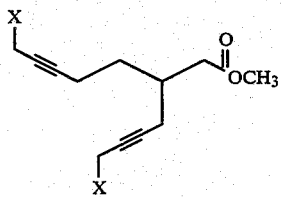

and said corresponding produced cyclic enediyne is:

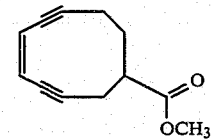

30. The process as defined in claim 27, wherein said propargylic halide is:

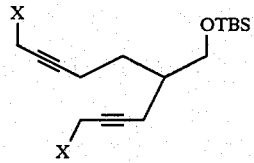

and said corresponding produced cyclic enediyne is:

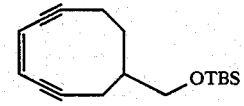

31. An enediyne having the following formula:

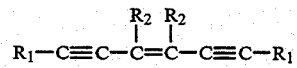

wherein $R_1$ and $R_2$ are nonfunctional groups, said enediyne being produced by the following process:
reacting a propargylic halide in the presence of a deprotonating base, a carbenoid destabilizing agent and a chelating agent to form said enediyne, said propargylic halide having the following formula:

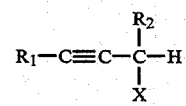

wherein X is Cl, Br or I and $R_1$ and $R_2$ are the same as above.

* * * * *

UNITED STATES PATENT AND TRADEMARK OFFICE
CERTIFICATE OF CORRECTION

PATENT NO. : 5,436,361
DATED : July 25, 1995
INVENTOR(S) : Graham B. Jones and Robert S. Huber It is certified that error appears in the above-indentified patent and that said Letters Patent is hereby corrected as shown below:

Column 14, line 62, please change 1,467 to 1.467.

Signed and Sealed this

Twenty-eighth Day of November 1995

Attest:

BRUCE LEHMAN

*Attesting Officer*      *Commissioner of Patents and Trademarks*